(12) United States Patent
Hori et al.

(10) Patent No.: US 9,907,308 B2
(45) Date of Patent: Mar. 6, 2018

(54) AQUEOUS SUSPENSION AGROCHEMICAL COMPOSITION

(71) Applicant: NISSAN CHEMICAL INDUSTRIES, LTD., Tokyo (JP)

(72) Inventors: Masahito Hori, Funabashi (JP); Hirokazu Kamatani, Funabashi (JP)

(73) Assignee: NISSAN CHEMICAL INDUSTRIES, LTD., Tokyo (JP)

( * ) Notice: Subject to any disclaimer, the term of this patent is extended or adjusted under 35 U.S.C. 154(b) by 0 days.

(21) Appl. No.: 15/646,447

(22) Filed: Jul. 11, 2017

(65) Prior Publication Data

US 2018/0014540 A1 Jan. 18, 2018

(30) Foreign Application Priority Data

Jul. 13, 2016 (JP) .................. 2016-138358

(51) Int. Cl.
*A01N 43/80* (2006.01)
*A01N 25/04* (2006.01)
*A01N 25/30* (2006.01)

(52) U.S. Cl.
CPC ............. *A01N 43/80* (2013.01); *A01N 25/04* (2013.01); *A01N 25/30* (2013.01)

(58) Field of Classification Search
CPC ......... A01N 43/80; A01N 25/04; A01N 25/30
USPC ....................................................... 514/378
See application file for complete search history.

(56) References Cited

FOREIGN PATENT DOCUMENTS

| WO | 99/02036 A1 | 1/1999 |
|----|-------------|--------|
| WO | 2007/026965 A1 | 3/2007 |
| WO | 2014/119519 A1 | 8/2014 |
| WO | 2014/126208 A1 | 8/2014 |
| WO | 2015/115488 A1 | 8/2015 |

OTHER PUBLICATIONS

English translation of WO 2015115488 (filed 2015).*

* cited by examiner

*Primary Examiner* — Yevgeny Valenrod
(74) *Attorney, Agent, or Firm* — Oliff PLC

(57) ABSTRACT

There is provided an aqueous suspension agrochemical composition including (Z)-4-[5-(3,5-dichlorophenyl)-5-trifluoromethyl-4,5-dihydroisoxazol-3-yl]-N-(methoxyiminomethyl)-2-methylbenzamide, a thickener, a surfactant, and water, which is excellent in homogeneity stability during storage, and simultaneously excellent in ease of discharge from a storage container. An aqueous suspension agrochemical composition comprising (a) (Z)-4-[5-(3,5-dichlorophenyl)-5-trifluoromethyl-4,5-dihydroisoxazol-3-yl]-N-(methoxyiminomethyl)-2-methylbenzamide, (b) xanthan gum, (c) a surfactant, and (d) water, wherein the xanthan gum is contained in an amount of 0.15 to 0.65% by mass in the aqueous suspension agrochemical composition. The surfactant is preferably one selected from the group consisting of polyoxyethylene styryl phenyl ethers, polyoxyethylene polyoxypropylene block polymers, and mixtures thereof.

8 Claims, No Drawings

AQUEOUS SUSPENSION AGROCHEMICAL COMPOSITION

TECHNICAL FIELD

The present invention relates to an aqueous suspension agrochemical composition comprising (Z)-4-[5-(3,5-dichlorophenyl)-5-trifluoromethyl-4,5-dihydroisoxazol-3-yl]-N-(methoxyimino methyl)-2-methylbenzamide (hereinafter referred to as "the compound A") as an agrochemical active ingredient, which is excellent in homogeneity stability during storage and ease of discharge from a storage container.

BACKGROUND ART

Specific isoxazoline-substituted benzamide compounds are known to have control activities against pests (for example, insects, mites, crustaceans, and nematodes) in the agricultural/horticultural field or livestock/sanitation field (see Patent Document 1, for example).

Aqueous suspension agrochemical compositions containing the compound A, a thickener, a surfactant, and water are also known (see Patent Documents 2 and 3, for example).

PRIOR ART DOCUMENTS

Patent Documents

[Patent Document 1] WO 2007/026965 A1
[Patent Document 2] WO 2014/126208 A1
[Patent Document 3] WO 2015/115488 A1

SUMMARY OF THE INVENTION

Problem to be Solved by the Invention

After an aqueous suspension agrochemical composition containing the compound A, a thickener, a surfactant, and water has been stored, it may become non-homogeneous due to the separation of supernatant. Furthermore, after a container filled with the aqueous suspension agrochemical composition has been stored, the aqueous suspension agrochemical composition may not be readily discharged from the container.

While the aqueous suspension agrochemical compositions disclosed in Patent Documents 2 and 3 are intended to achieve improved storage stability, they are not intended to achieve improved ease of discharge. Additionally, these patent documents do not suggest using the thickener to provide an effective means for preventing a decrease in homogeneity stability during storage and in ease of discharge from the storage container, and in particular, do not suggest setting the thickener content in a specific range to thereby prevent the aqueous suspension agrochemical composition during storage from becoming non-homogenous, and prevent difficulty in discharging the aqueous suspension agrochemical composition during storage from the container. In fact, it has been confirmed that in the aqueous suspension agrochemical composition disclosed in Patent Document 2, the thickener content described in Patent Document 2 cannot sufficiently effectively prevent the aqueous suspension agrochemical composition during storage from becoming non-homogeneous.

The present invention has been made to solve the aforementioned problem. An object of the present invention is to provide an aqueous suspension agrochemical composition that is excellent in homogeneity stability during storage and ease of discharge from a storage container.

Means for Solving the Problem

As a result of keen examination to solve the aforementioned problem, the present inventors have discovered that an aqueous suspension agrochemical composition that is excellent in homogeneity stability during storage and is simultaneously excellent in ease of discharge from a storage container can be provided by controlling the thickener content in a specific range.

Specifically, the present invention relates to an aqueous suspension agrochemical composition (hereinafter also referred to as "the composition of the present invention") set forth in [1] to [4] below.

[1]
An aqueous suspension agrochemical composition comprising (a) (Z)-4-[5-(3,5-dichlorophenyl)-5-trifluoromethyl-4,5-dihydroisoxazol-3-yl]-N-(methoxyimino methyl)-2-methylbenzamide, (b) xanthan gum, (c) a surfactant, and (d) water, wherein the xanthan gum is contained in an amount of 0.15 to 0.65% by mass in the aqueous suspension agrochemical composition.

[2]
The aqueous suspension agrochemical composition according to [1] above, wherein the xanthan gum is contained in an amount of 0.2 to 0.65% by mass in the aqueous suspension agrochemical composition.

[3]
The aqueous suspension agrochemical composition according to [1] or [2] above, wherein the surfactant (c) is one selected from the group consisting of polyoxyethylene styryl phenyl ethers, polyoxyethylene polyoxypropylene block polymers, and mixtures thereof.

[4]
The aqueous suspension agrochemical composition according to any one of [1] to [3] above, wherein the aqueous suspension agrochemical composition is a flowable formulation.

Effects of the Invention

The composition of the present invention is excellent in homogeneity stability during storage, and is simultaneously excellent in ease of discharge from a storage container.

MODES FOR CARRYING OUT THE INVENTION

The compound A contained in the composition of the present invention has a structure of formula (1) below, and is described in WO 2007/026965 A1, for example.

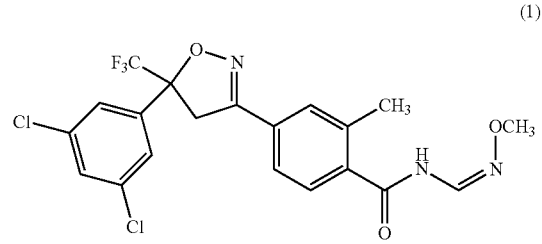 [SMILES: CO/N=C\NC(=O)c1ccc(C2=NOC(c3cc(Cl)cc(Cl)c3)(C(F)(F)F)C2)cc1C]

(1)

In the composition of the present invention, an organic solvent in which the compound A is poorly soluble or water can be used as a dispersion medium. Examples of such organic solvents include alcohol solvents such as ethylene glycol, diethylene glycol, propylene glycol, dipropylene glycol, and isopropanol; ethereal solvents such as butyl cellosolve; ketone solvents such as cyclohexanone; ester solvents such as γ-butyrolactone; acid amide solvents such as N-methylpyrrolidone and N-octylpyrrolidone; aromatic hydrocarbon solvents such as xylene, alkylbenzene, phenylxylylethane, and alkyl naphthalene; aliphatic hydrocarbon solvents such as machine oil, normal paraffin, isoparaffin, and naphthene; mixtures of aromatic hydrocarbon solvents and aliphatic hydrocarbon solvents, such as kerosene; and fats and oils such as soybean oil, linseed oil, rapeseed oil, coconut oil, cotton seed oil, and castor oil.

The amount of the compound A contained in the composition of the present invention is typically 0.1 to 50 parts by mass, per 100 parts by mass of the composition of the present invention. The lower limit of the amount is preferably 0.5% by mass or more, 1% by mass or more, 3% by mass or more, 4% by mass or more, or 5% by mass or more. The upper limit of the amount is preferably 40% by mass or less, 30% by mass or less, or 20% by mass or less.

The composition of the present invention may also contain, other than the compound A, additional one or more known agrochemicals such as a herbicide, an insecticide, a miticide, a nematicide, an antiviral agent, a plant growth regulator, a microbicide, an attractant, and a repellent, for example. A microbicide, a bactericide, a nematicide, a miticide, and an insecticide are preferred as known agrochemicals. Specific examples of general names thereof include, although not necessarily limited to, the following:

Microbicides: acibenzolar-S-methyl, acypetacs, aldimorph, allyl alcohol, ametoctradin, amisulbrom, amobam, ampropylfos, anilazine, azaconazole, azithiram, azoxystrobin, barium polysulfide, benalaxyl, benalaxyl-M, benodanil, benomyl, benquinox, bentaluron, benthiavalicarb-isopropyl, benthiazole, benzamacril, benzamorf, benzovindiflupyr, binapacryl, biphenyl, bitertanol, bixafen, blasticidin-S, bordeaux mixture, boscalid, bromoconazole, bupirimate, buthiobate, butylamine, calcium polysulfide, captafol, captan, carbamorph, carbendazim, carboxin, carpropamid, carvone, cheshunt mixture, chinomethionat, chlobenthiazone, chloraniformethane, chloranil, chlorfenazole, chloroneb, chloropicrin, chlorothalonil, chlorquinox, chlozolinate, climbazole, copper acetate, basic copper carbonate, copper hydroxide, copper naphthenate, copper oleate, copper oxychloride, copper sulfate, basic copper sulfate, copper zinc chromate, cresol, cufraneb, cuprobam, cyazofamid, cyclafuramid, cycloheximide, cyflufenamid, cymoxanil, cypendazole, cyproconazole, cyprodinil, cyprofuram, dazomet, debacarb, decafentin, dehydroacetic acid, dichlofluanid, dichlone, dichlorophen, dichlozoline, diclobutrazol, diclocymet, diclomezine, dicloran, diethofencarb, difenoconazole, diflumetorim, dimethirimol, dimethomorph, dimoxystrobin, diniconazole, diniconazole-M, dinobuton, dinocap, dinocap-4, dinocap-6, dinocton, dinosulfon, dinoterbon, diphenylamine, dipymetitrone, dipyrithione, disulfiram, ditalimfos, dithianon, DNOC, dodemorph, dodine, drazoxolon, edifenphos, enestrobin, epoxiconazole, ethaboxam, etaconazole, etem, ethirimol, ethoxyquin, etridiazole, famoxadone, fenamidone, fenaminosulf, fenapanil, fenarimol, fenbuconazole, fenfuram, fenhexamid, fenitropan, fenoxanil, fenpiclonil, fenpropidin, fenpropimorph, fenpyrazamine, fentin, ferbam, ferimzone, fluazinam, fludioxonil, flufenoxystrobin, flumetover, flumorph, fluopicolide, fluopyram, fluoroimide, fluotrimazole, fluoxastrobin, fluquinconazole, flusilazole, flusulfamide, flutolanil, flutianil, flutriafol, fluxapyroxad, folpet, fosetyl-aluminium, fthalide, fuberidazole, furalaxyl, furametpyr, furcarbanil, furconazole, furconazole-cis, furmecyclox, furophanate, glyodin, griseofulvin, guazatine, halacrinate, hexachlorobenzene, hexaconazole, hexylthiofos, 8-hydroxyquinoline sulfate, hymexazol, imazalil, imibenconazole, iminoctadine-albesilate, iminoctadine-triacetate, iodocarb, ipconazole, iprobenfos, iprodione, iprovalicarb, isofetamid, isotianil, isoprothiolane, isopyrazam, isovaledione, kasugamycin, kresoxim-methyl, laminarin, mancopper, mancozeb, mandestrobin, mandipropamid, maneb, mebenil, mecarbinzid, mepanipyrim, mepronil, metalaxyl, metalaxyl-M, metam, metazoxolon, metconazole, methasulfocarb, methfuroxam, metiram, metominostrobin, metrafenone, metsulfovax, milneb, myclobutanil, myclozolin, nabam, naftifine, natamycin, nickel bis(dimethyldithiocarbamate), nitrostyrene, nitrothal-isopropyl, nuarimol, octhilinone, ofurace, orysastrobin, oxadixyl, oxathiapiprolin, oxine copper, oxpoconazole fumarate, oxycarboxin, pefurazoate, penconazole, pencycuron, penflufen, pentachlorophenol (PCP), penthiopyrad, 2-phenylphenol, phosdiphen, phthalide, picarbutrazox, picoxystrobin, piperalin, polycarbamate, polyoxins, polyoxorim, potassium azide, potassium hydrogen carbonate, probenazole, prochloraz, procymidone, propamocarb hydrochloride, propiconazole, propineb, proquinazid, prothiocarb, pyrazophos, pyribencarb-methyl, pyrifenox, pyrimethanil, pyriminostrobin, pyroquilon, prothiocarb, prothioconazole, pydiflumetofen, pyracarbolid, pyraclostrobin, pyraziflumid, pyridinitril, pyriofenone, pyrisoxazole, pyroxychlor, pyroxyfur, quinacetol-sulfate, quinazamid, quinconazole, quinoxyfen, quintozene, rabenzazole, salicylanilide, sedaxane, silthiofam, simeconazole, sodium hydrogen carbonate, sodium hypochlorite, spiroxamine, sulfur, tebuconazole, tebufloquin, tecloftalam, tecnazene, tecoram, tetraconazole, thiabendazole, thiadifluor, thicyofen, thifluzamide, thiochlorfenphim, thiophanate, thiophanate-methyl, thiram, tiadinil, tioxymid, tolclofos-methyl, tolprocarb, tolylfluanid, triadimefon, triadimenol, triamiphos, triarimol, triazbutil, triazoxide, tributyltin oxide, trichlamide, tricyclazole, tridemorph, trifloxystrobin, triflumizole, triforine, triticonazole, validamycin, valifenalate, vinclozolin, zarilamid, zinc naphthenate, zinc sulfate, zineb, ziram, zoxamide, *Lentinula edodes* mycelia extract, *Lentinula edodes* fruiting body extract, MIF-1002 (test name), OAF-211 (test name), and SB-4303 (test name).

Bactericides: benzalkonium chloride, bithionol, bronopol, cresol, formaldehyde, nitrapyrin, oxolinic acid, oxyterracycline, streptomycin, and tecloftalam.

Nematicides: aldoxycarb, benclothiaz, cadusafos, DBCP, dichlofenthion, DSP, ethoprophos, fenamiphos, fensulfothion, fluazaindolizine, fluensulfone, fosthiazate, fosthietan, imicyafos, isamidofos, isazofos, oxamyl, thiaxazafen, thionazin, tioxazafen, BYI-1921 (test name), and MAI-08015 (test name).

Miticides: acequinocyl, acrinathrin, amidoflumet, amitraz, azocyclotin, BCI-033 (test name), benzoximate, bifenazate, bromopropylate, chinomethionat, chlorobezilate, clofentezine, cyenopyrafen, cyflumetofen, cyhexatine, dicofol, dienochlor, diflovidazin, DNOC, etoxazole, fenazaquin, fenbutatin oxide, fenothiocarb, fenpropathrin, fenpyroximate, fluacrypyrim, halfenprox, hexythiazox, milbemectin, propargite, pyflubumide, pyridaben, pyrimidifen, S-1870 (test name), spirodiclofen, spyromesifen, CL900167 (test name), tebufenpyrad, and NA-89 (test name).

Insecticides: abamectin, acephate, acetamipirid, afidopyropen, afoxolaner, alanycarb, aldicarb, allethrin, azamethiphos, azinphos-ethyl, azinphos-methyl, *bacillus thuringiensis*, bendiocarb, benfluthrin, benfuracarb, bensultap, bifenthrin, bioallethrin, bioresmethrin, bistrifluron, broflanilide, buprofezin, butocarboxim, carbaryl, carbofuran, carbosulfan, cartap, chlorantraniliprole, chlorethxyfos, chlorfenapyr, chlorfenvinphos, chlorfluazuron, chlormephos, chloroprallethrin, chlorpyrifos, chlorpyrifos-methyl, chromafenozide, clothianidin, cyanophos, cyantraniliprole, cyclaniliprole, cycloprothrin, cyflumetofen, cyfluthrin, beta-cyfluthrin, cyhalodiamide, cyhalothrin, gamma-cyhalothrin, lambda-cyhalothrin, cypermethrin, alpha-cypermethrin, beta-cypermethrin, zeta-cypermethrin, cyphenothrin, cyromazine, deltamethrin, diacloden, diafenthiuron, diazinon, dicloromezotiaz, dichlorvos, diflubenzuron, dimefluthrin, dimethylvinphos, dinotefuran, diofenolan, disulfoton, dimethoate, emamectin-benzoate, empenthrin, endosulfan, alpha-endosulfan, EPN, esfenvalerate, ethiofencarb, ethiprole, etofenprox, etrimfos, fenitrothion, fenobucarb, fenoxycarb, fenpropathrin, fenthion, fenvalerate, fipronil, flonicamid, fluazuron, flubendiamide, flucycloxuron, flucythrinate, flufenerim, flufenoxuron, flufenprox, flumethrin, fluralaner, fluvalinate, tau-fluvalinate, fonophos, formetanate, formothion, furathiocarb, flufiprole, fluhexafon, flupyradifurone, flometoquin, halofenozide, heptafluthrin, hexaflumuron, hydramethylnon, imidacloprid, imiprothrin, isofenphos, indoxacarb, indoxacarb-MP, isoprocarb, isoxathion, kappa-bifenthrin, kappa-tefluthrin, lepimectin, lufenuron, malathion, meperfluthrin, metaflumizone, metaldehyde, methamidophos, methidathion, methacrifos, metalcarb, methomyl, methoprene, methoxychlor, methoxyfenozide, methyl bromide, metofluthrin, epsilon-metofluthrin, momfluorothrin, epsilon-momfluorothrin, monocrotophos, muscalure, nitenpyram, novaluron, noviflumuron, omethoate, oxydemeton-methyl, oxydeprofos, parathion, parathion-methyl, pentachlorophenol, permethrin, phenothrin, phenthoate, phoxim, phorate, phosalone, phosmet, phosphamidon, pirimicarb, pirimiphos-methyl, profenofos, profluthrin, prothiofos, propaphos, protrifenbute, pymetrozine, pyraclofos, pyrethrins, pyridalyl, pyrifluquinazon, pyriprole, pyrafluprole, pyriproxyfen, resmethrin, rotenone, SI-0405 (test name), sulprofos, silafluofen, spinetoram, spinosad, spiromesifen, spirotetramat, sulfoxaflor, sulfotep, SYJ-159 (test name), tebfenozide, teflubenzuron, tefluthorin, terbufos, tetrachlorvinphos, tetramethrin, d-tetramethrin, tetramethylfluthrin, tetraniliprole, thiacloprid, thiocyclam, thiodicarb, thiamethoxam, thiofanox, thiometon, tolfenpyrad, tralomethrin, transfluthrin, triazamate, trichlorfon, triazuron, triflumezopyrim, triflumuron, vamidothion, MIE-1209 (test name), and ME5382 (test name).

Examples of surfactants used in the composition of the present invention include the following (A), (B), (C), (D), and (E).

(A) Nonionic surfactants:

(A-1) Polyethylene glycol-based surfactants: for example, a polyoxyethylene alkyl (for example, $C_{8-18}$) ether, an ethylene oxide adduct of an alkyl naphthol, a polyoxyethylene (mono or di)alkyl (for example, $C_{8-12}$) phenyl ether, a formalin condensate of a polyoxyethylene (mono or di)alkyl (for example, $C_{8-12}$) phenyl ether, a polyoxyethylene (mono, di, or tri)phenyl phenyl ether, a polyoxyethylene (mono, di, or tri)benzyl phenyl ether, a polyoxypropylene (mono, di, or tri)benzyl phenyl ether, a polyoxyethylene (mono, di, or tri)styryl phenyl ether, a polyoxypropylene (mono, di, or tri)styryl phenyl ether, a polymer of a polyoxyethylene (mono, di, or tri)styryl phenyl ether, a polyoxyethylene polyoxypropylene (mono, di, or tri)styryl phenyl ether, a polyoxyethylene polyoxypropylene block polymer, an alkyl (for example, $C_{8-18}$) polyoxyethylene polyoxypropylene block polymer ether, an alkyl (for example, $C_{8-12}$) phenyl polyoxyethylene polyoxypropylene block polymer ether, a polyoxyethylene bisphenyl ether, a polyoxyethylene resin acid ester, a polyoxyethylene fatty acid (for example, $C_{8-18}$) monoester, a polyoxyethylene fatty acid (for example, $C_{8-18}$) diester, a polyoxyethylene sorbitan (mono, di, or tri)fatty acid (for example, $C_{8-18}$) ester, a glycerol fatty acid ester ethylene oxide adduct, a castor oil ethylene oxide adduct, a hydrogenated castor oil ethylene oxide adduct, an alkyl (for example, $C_{8-18}$) amine ethylene oxide adduct, and a fatty acid (for example, $C_{8-18}$) amide ethylene oxide adduct.

(A-2) Polyhydric alcohol-based surfactants: for example, a glycerol fatty acid ester, a polyglycerin fatty acid ester, a pentaerythritol fatty acid ester, a sorbitol fatty acid (for example, $C_{8-18}$) ester, a sorbitan (mono, di, or tri)fatty acid (for example, $C_{8-18}$) ester, a sucrose fatty acid ester, a polyhydric alcohol alkyl ether, an alkyl glycoside, an alkyl polyglycoside, and a fatty acid alkanol amide.

(A-3) Acetylene-based surfactants: for example, acetylene glycol, acetylene alcohol, an ethylene oxide adduct of acetylene glycol, and an ethylene oxide adduct of acetylene alcohol.

(B) Anionic surfactants:

(B-1) Carboxylic acid-based surfactants: for example, carboxylic acids such as a poly(acrylic acid), a poly(methacrylic acid), a poly(maleic acid), a poly(maleic anhydride), a copolymer of maleic acid or maleic anhydride and an olefin (for example, isobutylene and diisobutylene), a copolymer of acrylic acid and itaconic acid, a copolymer of methacrylic acid and itaconic acid, a copolymer of maleic acid or maleic anhydride and styrene, a copolymer of acrylic acid and methacrylic acid, a copolymer of acrylic acid and methyl acrylate, a copolymer of acrylic acid and vinyl acetate, a copolymer of acrylic acid and maleic acid or maleic anhydride, a polyoxyethylene alkyl (for example, $C_{8-18}$) ether acetic acid, a N-methyl-fatty acid (for example, $C_{8-18}$) sarcosinate, and a resin acid and a fatty acid (for example, $C_{8-18}$), and salts of these carboxylic acids.

(B-2) Sulfuric acid ester-based surfactants: for example, sulfuric acid esters such as an alkyl (for example, $C_{8-18}$) sulfuric acid ester, a polyoxyethylene alkyl (for example, $C_{8-18}$) ether sulfuric acid ester, a polyoxyethylene (mono or di)alkyl (for example, $C_{8-12}$) phenyl ether sulfuric acid ester, a sulfuric acid ester of a polymer of a polyoxyethylene (mono or di)alkyl (for example, $C_{8-12}$) phenyl ether, a polyoxyethylene (mono, di, or tri)phenyl phenyl ether sulfuric acid ester, a polyoxyethylene (mono, di, or tri)benzyl phenyl ether sulfuric acid ester, a polyoxyethylene (mono, di, or tri)styryl phenyl ether sulfuric acid ester, a sulfuric acid ester of a polymer of a polyoxyethylene (mono, di, or tri)styryl phenyl ether, a sulfuric acid ester of a polyoxyethylene polyoxypropylene block polymer, a sulfonated oil, a sulfonated fatty acid ester, a sulfonated fatty acid, and a sulfonated olefin, and salts of these sulfuric acid esters.

(B-3) Sulfonic acid-based surfactants: for example, sulfonic acids such as a paraffin (for example, $C_{8-22}$) sulfonic acid, an alkyl (for example, $C_{8-16}$) benzene sulfonic acid, a formalin condensate of an alkyl (for example, $C_{8-16}$) benzene sulfonic acid, a formalin condensate of a cresol sulfonic acid, an α-olefin (for example, $C_{8-16}$) sulfonic acid, a dialkyl (for example, $C_{8-12}$) sulfosuccinic acid, a lignin sulfonic acid, a polyoxyethylene (mono or di)alkyl (for example, $C_{8-12}$) phenyl ether sulfonic acid, a polyoxyethylene alkyl (for example, $C_{8-18}$) ether sulfosuccinic acid half ester, a naphthalene sulfonic acid, a (mono or di)alkyl (for example, $C_{1-6}$) naphthalene sulfonic acid, a formalin condensate of a naphthalene sulfonic acid, a formalin condensate of a (mono or di)alkyl (for example, $C_{1-6}$) naphthalene sulfonic acid, a formalin condensate of a creosote oil sulfonic acid, an alkyl (for example, $C_{8-12}$) diphenyl ether disulfonic acid, Igepon T (trade name), a polystyrene sulfonic acid, and a copolymer of a styrene sulfonic acid and methacrylic acid, and salts of these sulfonic acids.

(B-4) Phosphoric acid ester-based surfactants: for example, phosphoric acid esters such as an alkyl (for example, $C_{8-12}$) phosphoric acid ester, a polyoxyethylene alkyl (for example, $C_{8-18}$) ether phosphoric acid ester, a polyoxyethylene (mono or di)alkyl (for example, $C_{8-12}$) phenyl ether phosphoric acid ester, a phosphoric acid ester of a polymer of a polyoxyethylene (mono, di, or tri)alkyl (for example, $C_{8-12}$) phenyl ether, a polyoxyethylene (mono, di, or tri)phenyl phenyl ether phosphoric acid ester, a polyoxyethylene (mono, di, or tri)benzyl phenyl ether phosphoric acid ester, a polyoxyethylene (mono, di, or tri)styryl phenyl ether phosphoric acid ester, a phosphoric acid ester of a polymer of a polyoxyethylene (mono, di, or tri)styryl phenyl ether, a phosphoric acid ester of a polyoxyethylene polyoxypropylene block polymer, phosphatidylcholine, phosphatidyl ethanol imine, and a condensed phosphoric acid (for example, tripolyphosphoric acid), and salts of these phosphoric acid esters.

Examples of counter ions of the salts in (B-1) to (B-4) above include alkali metals (lithium, sodium, potassium, and the like), alkaline earth metals (calcium, magnesium, and the like), ammonium and various amines (for example, an alkylamine, a cycloalkylamine, and an alkanol amine).

(C) Cationic surfactants: For example, an alkylamine, an alkyl quaternary ammonium salt, an ethylene oxide adduct of an alkylamine, and an ethylene oxide adduct of an alkyl quaternary ammonium salt.

(D) Amphoteric surfactants:

(D-1) Betaine-based surfactants: for example, an alkyl (for example, $C_{8-18}$) dimethylaminoacetic acid betaine, an acyl (for example, $C_{8-18}$) aminopropyldimethylaminoacetic acid betaine, an alkyl (for example, $C_{8-18}$) hydroxysulfobetaine, and a 2-alkyl (for example, $C_{8-18}$)—N-carboxymethyl-N-hydroxyethylimidazolinium betaine.

(D-2) Amino acid-based surfactants: for example, an alkyl (for example, $C_{8-18}$) aminopropionic acid, an alkyl (for example, $C_{8-18}$) aminodipropionic acid, and a N-acyl (for example, $C_{8-18}$)—N'-carb oxyethyl-N'-hydroxyethylethylene diamine.

(D-3) Amine oxide-based surfactants: for example, an alkyl (for example, $C_{8-18}$) dimethylamine oxide and an acyl (for example, $C_{8-18}$) aminopropyldimethylamine oxide.

(E) Other surfactants:

(E-1) Silicone-based surfactants: for example, a polyoxyethylene-methylpolysiloxane copolymer, a polyoxypropylene-methylpolysiloxane copolymer, and a poly(oxyethylene-oxypropylene)-methylpolysiloxane copolymer.

(E-2) Fluorine-based surfactants: for example, a perfluoroalkenyl benzene sulfonate, a perfluoroalkyl sulfonate, a perfluoroalkyl carboxylate, a perfluoroalkenyl polyoxyethylene ether, a perfluoroalkyl polyoxyethylene ether, and a perfluoroalkyl trimethyl ammonium salt.

As used herein, the recitation "$C_a$-$C_b$ alkyl" or "alkyl $(C_a$-$C_b)$" represents a linear or branched hydrocarbon group having a carbon atom number of a to b. Specific examples thereof include methyl group, ethyl group, n-propyl group, i-propyl group, n-butyl group, i-butyl group, t-butyl group, s-butyl group, 1-pentyl group, 1-methylbutyl group, 2-methylbutyl group, 3-methylbutyl group, 1-ethylpropyl group, 1,1-dimethylpropyl group, 1,2-dimethylpropyl group, neopentyl group, 1-hexyl group, 1-methylpentyl group, 2-methylpentyl group, 3-methylpentyl group, 4-methylpentyl group, 1-ethylbutyl group, 2-ethylbutyl group, 1,1-dimethylbutyl group, 1,2-dimethylbutyl group, 1,3-dimethylbutyl group, 2,2-dimethylbutyl group, 2,3-dimethylbutyl group, 3,3-dimethylbutyl group, 1,1,2-trimethylpropyl group, 1-ethyl-1-methylpropyl group, 1-ethyl-2-methylpropyl group, 1-heptyl group, 1-octyl group, 2-ethylhexyl group, 1-nonyl group, 1-decyl group, 1-undecyl group, 1-dodecyl group, 1-tridecyl group, 1-tetradecyl group, 1-pentadecyl group, 1-hexadecyl group, 1-heptadecyl group, 1-octadecyl group, 1-nonadecyl group, 1-icosyl group, and 1-henicosyl group. An alkyl group whose carbon number is in each designated range is selected. The symbols n-, s-, and t- mean normal, iso, secondary, and tertiary, respectively.

These surfactants can be used alone or as a mixture of two or more, and the ratio of the mixture can be freely selected. Preferred examples include polyoxyethylene styryl phenyl ethers, polyoxyethylene polyoxypropylene block polymers, and mixtures thereof. While the amount of the surfactant contained in the composition of the present invention may be selected as appropriate, it is typically 0.01 to 20 parts by mass per 100 parts by mass of the composition of the present invention. The lower limit of the amount is preferably 0.1 part by mass or more, and more preferably 0.5 part by mass or more. The upper limit of the amount is preferably 15 parts by mass or less, and more preferably 10 parts by mass or less.

The thickener to be used may be an organic or inorganic natural product, or a synthetic or semi-synthetic product. Examples of organic thickeners include polysaccharides such as xanthan gum, welan gum, and rhamsan gum; water-soluble polymer compounds such as polyvinyl alcohol, polyvinyl pyrrolidone, polyacrylic acid, sodium polyacrylate, and polyacrylamide; and cellulose derivatives such as methyl cellulose, carboxymethyl cellulose, carboxyethyl cellulose, hydroxyethyl cellulose, and hydroxypropylcellulose. Examples of inorganic thickeners include smectite clay minerals such as montmorillonite, saponite, hectorite, bentonite, laponite, and synthetic smectite. Preferred examples include xanthan gum and smectite clay minerals. These thickeners may be used alone or as a mixture of two or more, and the ratio of the mixture can be freely selected. These thickeners may be directly used, or may be dispersed or dissolved in water before use. The amount of the thickener contained in the composition of the present invention can be freely selected. The lower limit of the amount is typically 0.15 part by mass or more, or 0.2 part by mass or more, per 100 parts by mass of the composition of the present invention. The upper limit of the amount is typically 0.65 part by mass or less per 100 parts by mass of the composition of the present invention.

The composition of the present invention may further contain various auxiliary agents. Examples of auxiliary agents include anti-freezing agents, anti-foaming agents, anti-bacterial/anti-fungal agents, and colorants.

Examples of anti-freezing agents include ethylene glycol, diethylene glycol, propylene glycol, and glycerin. Preferred are propylene glycol and glycerin. The amount of the anti-freezing agent contained in the composition of the present invention can be freely selected.

Examples of anti-foaming agents include silicone-based emulsions.

The composition of the present invention has excellent homogeneity stability during storage. The homogeneity stability during storage can be evaluated by the following "supernatant separation measurement test".

The composition of the present invention or a composition as a control is placed in a glass bottle having a diameter of 3 cm and a height of 5 cm so that the liquid surface is positioned at a height of 4.5 cm from the bottom. The glass bottle is then sealed with a cap, and stored in a thermostat at 54° C. for 2 weeks. With regard to the supernatant after storage (transparent layer formed in an upper section), assuming that the height from the bottom of the glass bottle to the upper edge of the composition is $X_1$ cm, and the height of the supernatant after storage is $Y_1$ cm, the separation of supernatant is calculated based on the following equation:

Separation (%)=$(Y_1/X_1)\times 100$

In the composition of the present invention, the separation of supernatant is preferably 20% or less, and more preferably 0%.

The composition of the present invention also has excellent ease of discharge from a storage container. The ease of discharge from a storage container can be evaluated by the following "ease-of-discharge measurement test".

Fifteen grams of the composition of the present invention or a composition as a control is placed in a glass bottle having a diameter of 3 cm and a height of 5 cm. The glass bottle is then sealed with a cap, and stored in a thermostat at 25° C. for 1 day. The glass bottle after storage is inverted 10 times, and after the cap is removed, the composition is discharged by inverting the glass bottle for 1 minute. Assuming that the mass of the composition filled in the glass bottle is $X_2$ g, and the mass of the composition discharged is $Y_2$ g, the discharge ratio is calculated based on the following equation:

Discharge ratio (%)=$(Y_2/X_2)\times 100$

The composition of the present invention preferably has a discharge ratio of the composition of 80% or more.

Examples of dosage forms of the composition of the present invention include a flowable formulation (suspension concentrate) and a suspoemulsion.

The method for producing the composition of the present invention is not limited to a particular method; for example, it may be produced by adding the components described above to a dispersion medium, and mixing them with a stirrer. As required, the agrochemical active ingredient, the surfactant, and other auxiliary agents, each independently or as a mixture, may be pulverized in a dry or wet grinding machine.

Dry grinding can be performed using a hammer mill, a pin mill, a jet mill, a ball mill, or a roll mill, for example. Pulverization by wet grinding can be performed using a wet grinding machine such as an in-line mill or a bead mill, for example.

Formulation examples of the composition of the present invention will be illustrated below, although the present invention is not limited thereto. In the following description, "parts" means parts by mass.

Formulation Example 1

| | |
|---|---|
| Compound A as an active ingredient (purity: 94.0%) | 6.3 parts |
| Mixture of a polyoxyethylene nonylphenyl ether and dioctyl sulfosuccinate sodium salt | 7.0 parts |
| Dioctyl sulfosuccinate sodium salt | 5.0 parts |
| Montmorillonite | 0.2 part |

-continued

| | |
|---|---|
| Propylene glycol | 7.0 parts |
| Silicone-based anti-foaming agent | 0.2 part |
| Anti-bacterial/anti-fungal agent | 0.1 part |
| Xanthan gum | 0.2 part |
| Water | 74.0 parts |

The above-listed components were homogeneously mixed and then subjected to wet grinding, thus obtaining an aqueous suspension agrochemical composition.

Formulation Example 2

| | |
|---|---|
| Compound A as an active ingredient (purity: 94.0%) | 6.3 parts |
| Polyoxyethylene tridecyl ether | 2.0 parts |
| Mixture of an acrylic copolymer and propylene glycol | 3.0 parts |
| Bentonite | 0.3 part |
| Propylene glycol | 7.0 parts |
| Silicone-based anti-foaming agent | 0.2 part |
| Anti-bacterial/anti-fungal agent | 0.1 part |
| Xanthan gum | 0.4 part |
| Water | 80.7 parts |

The above-listed components were homogeneously mixed and then subjected to wet grinding, thus obtaining an aqueous suspension agrochemical composition.

Formulation Example 3

| | |
|---|---|
| Compound A as an active ingredient (purity: 94.0%) | 6.3 parts |
| Polyoxyethylene aryl phenyl ether sulfate | 7.0 parts |
| 2,4,7,9-Tetramethyl-5-decyne-4,7-diol | 0.2 part |
| Montmorillonite | 0.2 part |
| Propylene glycol | 7.0 parts |
| Silicone-based anti-foaming agent | 0.2 part |
| Anti-bacterial/anti-fungal agent | 0.1 part |
| Xanthan gum | 0.2 part |
| Water | 78.8 parts |

The above-listed components were homogeneously mixed and then subjected to wet grinding, thus obtaining an aqueous suspension agrochemical composition.

Formulation Example 4

| | |
|---|---|
| Compound A as an active ingredient (purity: 94.0%) | 6.3 parts |
| Polyoxyethylene aryl phenyl ether phosphate | 7.0 parts |
| 2,4,7,9-Tetramethyl-5-decyne-4,7-diol | 0.2 part |
| Montmorillonite | 0.2 part |
| Propylene glycol | 7.0 parts |
| Silicone-based anti-foaming agent | 0.2 part |
| Anti-bacterial/anti-fungal agent | 0.1 part |
| Xanthan gum | 0.2 part |
| Water | 78.8 parts |

The above-listed components were homogeneously mixed and then subjected to wet grinding, thus obtaining an aqueous suspension agrochemical composition.

Formulation Example 5

| | |
|---|---|
| Compound A as an active ingredient (purity: 94.0%) | 6.3 parts |
| Methylnaphthalene sulfonate formalin condensate | 0.1 part |
| 2,4,7,9-Tetramethyl-5-decyne-4,7-diol | 0.2 part |
| Montmorillonite | 0.2 part |
| Propylene glycol | 7.0 parts |
| Silicone-based anti-foaming agent | 0.2 part |
| Anti-bacterial/anti-fungal agent | 0.1 part |
| Xanthan gum | 0.2 part |
| Water | 85.7 parts |

The above-listed components were homogeneously mixed and then subjected to wet grinding, thus obtaining an aqueous suspension agrochemical composition.

Formulation Example 6

| | |
|---|---|
| Compound A as an active ingredient (purity: 94.0%) | 6.3 parts |
| Polycarboxylate | 0.1 part |
| 2,4,7,9-Tetramethyl-5-decyne-4,7-diol | 0.2 part |
| Montmorillonite | 0.2 part |
| Propylene glycol | 7.0 parts |
| Silicone-based anti-foaming agent | 0.2 part |
| Anti-bacterial/anti-fungal agent | 0.1 part |
| Xanthan gum | 0.2 part |
| Water | 85.7 parts |

The above-listed components were homogeneously mixed and then subjected to wet grinding, thus obtaining an aqueous suspension agrochemical composition.

Formulation Example 7

| | |
|---|---|
| Compound A as an active ingredient (purity: 94.0%) | 6.3 parts |
| Alkyl benzene sulfonate | 0.1 part |
| 2,4,7,9-Tetramethyl-5-decyne-4,7-diol | 0.2 part |
| Montmorillonite | 0.2 part |
| Propylene glycol | 7.0 parts |
| Silicone-based anti-foaming agent | 0.2 part |
| Anti-bacterial/anti-fungal agent | 0.1 part |
| Xanthan gum | 0.2 part |
| Water | 85.7 parts |

The above-listed components were homogeneously mixed and then subjected to wet grinding, thus obtaining an aqueous suspension agrochemical composition.

Formulation Example 8

| | |
|---|---|
| Compound A as an active ingredient (purity: 94.0%) | 6.3 parts |
| Phenol sulfonate formaldehyde condensate | 0.1 part |
| 2,4,7,9-Tetramethyl-5-decyne-4,7-diol | 0.2 part |
| Montmorillonite | 0.2 part |
| Propylene glycol | 7.0 parts |
| Silicone-based anti-foaming agent | 0.2 part |
| Anti-bacterial/anti-fungal agent | 0.1 part |
| Xanthan gum | 0.2 part |
| Water | 85.7 parts |

The above-listed components were homogeneously mixed and then subjected to wet grinding, thus obtaining an aqueous suspension agrochemical composition.

The composition of the present invention may be applied by, for example, a method that involves applying the stock solution or a solution prepared by diluting approximately 50 to 5,000-fold with water to crops or trees or to soil on which they grow, using a sprayer, for example. Alternatively, the composition of the present invention may be applied by, for example, a method that involves applying the stock solution or a solution prepared by diluting approximately 2 to 100-fold with water from the air using a helicopter, for example.

EXAMPLES

The present invention will be hereinafter described in further detail with reference to examples, comparative examples, and test examples, to which the present invention is not limited. In the following description, "parts" means parts by mass.

Example 1

1. Preparation of a Ground Slurry

In 6.26 parts of water, 3 parts of a mixture of a polyoxyethylene styryl phenyl ether and a polyoxyethylene polyoxypropylene block polymer (trade name: SORPOL 3353; Toho Chemical Industry Co., Ltd.), 0.1 part of a silicone-based anti-foaming agent (trade name: KM-73; Shin-Etsu Chemical Co., Ltd.), 10 parts of propylene glycol, and 10.64 parts of the compound A as an active ingredient (purity: 94.0%) were dispersed, and then the dispersion was subjected to wet grinding in a sand grinder (AIMEX Co., Ltd.) using 200 g of glass beads with a diameter of 0.8 to 1.2 mm, thus obtaining 30 parts of a ground slurry.

2. Preparation of a Dispersion Medium

In 69.45 parts of water, 0.05 part of 1,2-benzisothiazolin-3-one (trade name: PROXEL GXL; Avecia Inc.), 0.2 part of xanthan gum (trade name: KELZAN S; CP Kelco, Inc.), and 0.3 part of smectite clay (trade name: VEEGUM R; R. T. Vanderbilt, Inc.) were dispersed in the mentioned order, thus obtaining 70 parts of a dispersion medium.

3. Preparation of an Aqueous Suspension Agrochemical Composition

Thirty parts of the ground slurry and 70 parts of the dispersion medium were mixed, thus obtaining 100 parts of a homogeneous aqueous suspension agrochemical composition.

Example 2

An aqueous suspension agrochemical composition was obtained as in Example 1, except that in the dispersion medium of Example 1, 69.45 parts of water was changed to 69.40 parts, and 0.2 part of xanthan gum (trade name: KELZAN S; CP Kelco, Inc.) was changed to 0.25 part.

Example 3

An aqueous suspension agrochemical composition was obtained as in Example 1, except that in the dispersion medium of Example 1, 69.45 parts of water was changed to 69.35 parts, and 0.2 part of xanthan gum (trade name: KELZAN S; CP Kelco, Inc.) was changed to 0.3 part.

Example 4

An aqueous suspension agrochemical composition was obtained as in Example 1, except that in the dispersion medium of Example 1, 69.45 parts of water was changed to 69.25 parts, and 0.2 part of xanthan gum (trade name: KELZAN S; CP Kelco, Inc.) was changed to 0.4 part.

Example 5

An aqueous suspension agrochemical composition was obtained as in Example 1, except that in the dispersion medium of Example 1, 69.45 parts of water was changed to 69.15 parts, and 0.2 part of xanthan gum (trade name: KELZAN S; CP Kelco, Inc.) was changed to 0.5 part.

Example 6

An aqueous suspension agrochemical composition was obtained as in Example 1, except that in the dispersion medium of Example 1, 69.45 parts of water was changed to 69.05 parts, and 0.2 part of xanthan gum (trade name: KELZAN S; CP Kelco, Inc.) was changed to 0.6 part.

Example 7

1. Preparation of a Ground Slurry

In 12.26 parts of water, 2 parts of a mixture of a polyoxyethylene styryl phenyl ether and a polyoxyethylene polyoxypropylene block polymer (trade name: SORPOL 3353; Toho Chemical Industry Co., Ltd.), 0.1 part of a silicone-based anti-foaming agent (trade name: KM-73; Shin-Etsu Chemical Co., Ltd.), 5 parts of propylene glycol, and 10.64 parts of the compound A as an active ingredient (purity: 94.0%) were dispersed, and then the dispersion was subjected to wet grinding in a sand grinder (AIMEX Co., Ltd.) using 200 g of glass beads with a diameter of 0.8 to 1.2 mm, thus obtaining 30 parts of a ground slurry.

2. Preparation of a Dispersion Medium

In 69.35 parts of water, 0.1 part of 1,2-benzisothiazolin-3-one (trade name: PROXEL GXL; Avecia Inc.), 0.25 part of xanthan gum (trade name: KELZAN S; CP Kelco, Inc.), and 0.3 part of smectite clay (trade name: VEEGUM R; R. T. Vanderbilt, Inc.) were dispersed in the mentioned order, thus obtaining 70 parts of a dispersion medium.

3. Preparation of an Aqueous Suspension Agrochemical Composition

Thirty parts of the ground slurry and 70 parts of the dispersion medium were mixed, thus obtaining 100 parts of a homogeneous aqueous suspension agrochemical composition.

Example 8

An aqueous suspension agrochemical composition was obtained as in Example 7, except that in the dispersion medium of Example 7, 69.35 parts of water was changed to 69.30 parts, and 0.25 part of xanthan gum (trade name: KELZAN S; CP Kelco, Inc.) was changed to 0.3 part.

Example 9

An aqueous suspension agrochemical composition was obtained as in Example 7, except that in the dispersion medium of Example 7, 69.35 parts of water was changed to 69.20 parts, and 0.25 part of xanthan gum (trade name: KELZAN S; CP Kelco, Inc.) was changed to 0.4 part.

Example 10

An aqueous suspension agrochemical composition was obtained as in Example 7, except that in the dispersion medium of Example 7, 69.35 parts of water was changed to 69.40 parts, and 0.25 part of xanthan gum (trade name: KELZAN S; CP Kelco, Inc.) was changed to 0.2 part of xanthan gum (trade name: KELZAN; CP Kelco, Inc.).

Example 11

An aqueous suspension agrochemical composition was obtained as in Example 7, except that in the dispersion medium of Example 7, 0.25 part of xanthan gum (trade name: KELZAN S; CP Kelco, Inc.) was changed to 0.25 part of xanthan gum (trade name: KELZAN; CP Kelco, Inc.).

Example 12

An aqueous suspension agrochemical composition was obtained as in Example 8, except that in the dispersion medium of Example 8, 0.3 part of xanthan gum (trade name: KELZAN S; CP Kelco, Inc.) was changed to 0.3 part of xanthan gum (trade name: KELZAN; CP Kelco, Inc.).

Example 13

An aqueous suspension agrochemical composition was obtained as in Example 12, except that 69.30 parts of water in Example 12 was changed to 69.25 parts, and 0.3 part of xanthan gum (trade name: KELZAN; CP Kelco, Inc.) in the dispersion medium was changed to 0.35 part.

Comparative Example 1

1. Preparation of a Ground Slurry

In 56.86 parts of water, 3 parts of a mixture of a polyoxyethylene styryl phenyl ether and a polyoxyethylene polyoxypropylene block polymer (trade name: SORPOL 3353; Toho Chemical Industry Co., Ltd.), 0.1 part of a silicone-based anti-foaming agent (trade name: KM-73; Shin-Etsu Chemical Co., Ltd.), 10 parts of propylene glycol, and 10.04 parts of the compound A as an active ingredient (purity: 99.6%) were dispersed, and then the dispersion was subjected to wet grinding in a sand grinder (AIMEX Co., Ltd.) using 200 g of glass beads with a diameter of 0.8 to 1.2 mm, thus obtaining 80 parts of a ground slurry.

2. Preparation of a Dispersion Medium

In 19.55 parts of water, 0.05 part of 1,2-benzisothiazolin-3-one (trade name: PROXEL GXL; Avecia Inc.), 0.1 part of xanthan gum (trade name: KELZAN ASX; CP Kelco, Inc.), and 0.3 part of smectite clay (trade name: VEEGUM R; R. T. Vanderbilt, Inc.) were dispersed in the mentioned order, thus obtaining 20 parts of a dispersion medium.

3. Preparation of an Aqueous Suspension Agrochemical Composition

Eighty parts of the ground slurry and 20 parts of the dispersion medium were mixed, thus obtaining 100 parts of a homogeneous aqueous suspension agrochemical composition.

Comparative Example 2

1. Preparation of a Ground Slurry

In 6.86 parts of water, 3 parts of a mixture of a polyoxyethylene styryl phenyl ether and a polyoxyethylene polyoxypropylene block polymer (trade name: SORPOL 3353; Toho Chemical Industry Co., Ltd.), 0.1 part of a silicone-based anti-foaming agent (trade name: KM-73; Shin-Etsu Chemical Co., Ltd.), 10 parts of propylene glycol, and 10.04 parts of the compound A as an active ingredient (purity:

99.6%) were dispersed, and then the dispersion was subjected to wet grinding in a sand grinder (AIMEX Co., Ltd.) using 200 g of glass beads with a diameter of 0.8 to 1.2 mm, thus obtaining 30 parts of a ground slurry.

2. Preparation of a Dispersion Medium

In 69.55 parts of water, 0.05 part of 1,2-benzisothiazolin-3-one (trade name: PROXEL GXL; Avecia Inc.), 0.1 part of xanthan gum (trade name: KELZAN ASX; CP Kelco, Inc.), and 0.3 part of smectite clay (trade name: VEEGUM R; R.T. Vanderbilt, Inc.) were dispersed in the mentioned order, thus obtaining 70 parts of a dispersion medium.

3. Preparation of an Aqueous Suspension Agrochemical Composition

Thirty parts of the ground slurry and 70 parts of the dispersion medium were mixed, thus obtaining 100 parts of a homogeneous aqueous suspension agrochemical composition.

Comparative Example 3

An aqueous suspension agrochemical composition was obtained as in Example 1, except that in the dispersion medium of Example 1, 69.45 parts of water was changed to 69.55 parts, and 0.2 part of xanthan gum (trade name: KELZAN S; CP Kelco, Inc.) was changed to 0.1 part.

Comparative Example 4

An aqueous suspension agrochemical composition was obtained as in Example 1, except that in the dispersion medium of Example 1, 69.45 parts of water was changed to 68.95 parts, and 0.2 part of xanthan gum (trade name: KELZAN S; CP Kelco, Inc.) was changed to 0.7 part.

[Test Example 1] Measurement of Supernatant Separation

The homogeneity stability of the compositions obtained in Examples 1 to 13 and Comparative Examples 1 to 3 was evaluated by the "supernatant separation measurement test" described above, and the separation (%) of supernatant of each composition was calculated.

The results are shown in Table 1.

TABLE 1

|  | Supernatant Separation (%) |
| --- | --- |
| Example 1 | 6 |
| Example 2 | 0 |
| Example 3 | 0 |
| Example 4 | 0 |
| Example 5 | 0 |
| Example 6 | 0 |
| Example 7 | 0 |
| Example 8 | 0 |
| Example 9 | 0 |
| Example 10 | 14 |
| Example 11 | 0 |
| Example 12 | 0 |
| Example 13 | 0 |
| Comparative Example 1 | 59 |
| Comparative Example 2 | 53 |
| Comparative Example 3 | 62 |

[Test Example 2] Measurement of Ease of Discharge

The compositions obtained in Examples 1 to 13 and Comparative Example 4 were evaluated by the "ease-of-discharge measurement test" described above, and the discharge ratio (%) of each composition was calculated.

The results are shown in Table 2. The symbols used in the table have the following meanings:
○: a discharge ratio of 80% or more
x: a discharge ratio of less than 80%

TABLE 2

|  | Discharge Ratio |
| --- | --- |
| Example 1 | ○ |
| Example 2 | ○ |
| Example 3 | ○ |
| Example 4 | ○ |
| Example 5 | ○ |
| Example 6 | ○ |
| Example 7 | ○ |
| Example 8 | ○ |
| Example 9 | ○ |
| Example 10 | ○ |
| Example 11 | ○ |
| Example 12 | ○ |
| Example 13 | ○ |
| Comparative Example 4 | x |

INDUSTRIAL APPLICABILITY

According to the present invention, the aqueous suspension agrochemical composition containing the compound A is excellent in homogeneity stability during storage and ease of discharge from a storage container, and is useful as a pest control agent.

The invention claimed is:

1. An aqueous suspension agrochemical composition comprising (a) (Z)-4-[5-(3,5-dichlorophenyl)-5-trifluoromethyl-4,5-dihydroisoxazol-3-yl]-N-(methoxyiminomethyl)-2-methylbenzamide, (b) xanthan gum, (c) a surfactant, and (d) water, wherein the xanthan gum is contained in an amount of 0.15 to 0.65% by mass in the aqueous suspension agrochemical composition.

2. The aqueous suspension agrochemical composition according to claim 1, wherein the xanthan gum is contained in an amount of 0.2 to 0.65% by mass in the aqueous suspension agrochemical composition.

3. The aqueous suspension agrochemical composition according to claim 1, wherein the surfactant (c) is one selected from the group consisting of polyoxyethylene styryl phenyl ethers, polyoxyethylene polyoxypropylene block polymers, and mixtures thereof.

4. The aqueous suspension agrochemical composition according to claim 1, wherein the aqueous suspension agrochemical composition is a flowable formulation.

5. The aqueous suspension agrochemical composition according to claim 2, wherein the surfactant (c) is one selected from the group consisting of polyoxyethylene styryl phenyl ethers, polyoxyethylene polyoxypropylene block polymers, and mixtures thereof.

6. The aqueous suspension agrochemical composition according to claim 2, wherein the aqueous suspension agrochemical composition is a flowable formulation.

7. The aqueous suspension agrochemical composition according to claim 3, wherein the aqueous suspension agrochemical composition is a flowable formulation.

8. The aqueous suspension agrochemical composition according to claim 5, wherein the aqueous suspension agrochemical composition is a flowable formulation.

* * * * *